US012623043B2

(12) United States Patent
Tsuji

(10) Patent No.: US 12,623,043 B2
(45) Date of Patent: May 12, 2026

(54) CPAP APPARATUS

(71) Applicant: Murata Manufacturing Co., Ltd., Kyoto (JP)

(72) Inventor: Shigeru Tsuji, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 1170 days.

(21) Appl. No.: 17/462,264

(22) Filed: Aug. 31, 2021

(65) Prior Publication Data

US 2021/0393914 A1 Dec. 23, 2021

Related U.S. Application Data

(63) Continuation of application No. PCT/JP2020/012250, filed on Mar. 19, 2020.

(30) Foreign Application Priority Data

Apr. 23, 2019 (JP) ................................ 2019-082052

(51) Int. Cl.
*A61M 16/10* (2006.01)
*A61M 16/00* (2006.01)

(52) U.S. Cl.
CPC ...... *A61M 16/109* (2014.02); *A61M 16/0003* (2014.02); *A61M 16/0066* (2013.01);
(Continued)

(58) Field of Classification Search
CPC .............. A61M 16/1045; A61M 16/1075–109
See application file for complete search history.

(56) References Cited

U.S. PATENT DOCUMENTS 6,435,180 B1 * 8/2002 Hewson ................ A61M 16/16
128/203.12
6,718,974 B1 * 4/2004 Moberg ................ A61M 16/16
128/204.14
(Continued)

FOREIGN PATENT DOCUMENTS

JP 2007-117650 A 5/2007
JP 2007-512876 A 5/2007
(Continued)

OTHER PUBLICATIONS

International Search Report for PCT/JP2020/012250 dated Apr. 21, 2020.
(Continued)

*Primary Examiner* — Joseph D. Boecker
*Assistant Examiner* — Thomas W Greig
(74) *Attorney, Agent, or Firm* — McDonald Hopkins LLC

(57) ABSTRACT

According to the present disclosure, a CPAP apparatus that has a humidification function and that has high portability is provided. A CPAP apparatus includes a body unit and a base unit on and from which the body unit is mountable and removable. The body unit includes a first housing that has a first inlet and a first outlet, an air-sending device that discharges, via the first outlet, air that is introduced via the first inlet, and a first control unit that controls the air-sending device. The base unit includes a second housing that has a second inlet and a second outlet, a humidifier that humidifies air that is introduced via the second inlet, and a second control unit that controls the humidifier.

12 Claims, 8 Drawing Sheets

(52) U.S. Cl.
CPC ... *A61M 16/024* (2017.08); *A61M 2016/0027* (2013.01); *A61M 2016/0039* (2013.01); *A61M 2205/3368* (2013.01); *A61M 2209/084* (2013.01)

(56) References Cited

U.S. PATENT DOCUMENTS

| | | | | |
|---|---|---|---|---|
| 7,413,173 | B2 * | 8/2008 | DiMatteo | A61M 16/16 |
| | | | | 261/119.1 |
| 9,884,163 | B2 * | 2/2018 | Mayer | A61M 16/0858 |
| 2003/0066526 | A1 * | 4/2003 | Thudor | A61M 16/161 |
| | | | | 128/203.26 |
| 2004/0055597 | A1 * | 3/2004 | Virr | A61M 16/16 |
| | | | | 128/203.12 |
| 2006/0113690 | A1 * | 6/2006 | Huddart | A61M 16/1075 |
| | | | | 261/129 |
| 2007/0068810 | A1 | 3/2007 | Tsukashima et al. | |
| 2007/0169776 | A1 * | 7/2007 | Kepler | A61M 16/107 |
| | | | | 128/200.14 |
| 2007/0193580 | A1 * | 8/2007 | Feldhahn | A61M 16/107 |
| | | | | 128/204.18 |
| 2008/0302362 | A1 * | 12/2008 | Kwok | A61M 16/161 |
| | | | | 128/203.16 |
| 2009/0120438 | A1 | 5/2009 | Chalvignac | |
| 2011/0120462 | A1 | 5/2011 | Tatkov et al. | |
| 2011/0253136 | A1 * | 10/2011 | Sweeney | A61M 16/024 |
| | | | | 128/207.18 |
| 2011/0308518 | A1 | 12/2011 | McGroary et al. | |
| 2014/0283831 | A1 | 9/2014 | Foote et al. | |
| 2017/0211438 | A1 | 7/2017 | Suzuki et al. | |
| 2017/0239433 | A1 * | 8/2017 | Martin | A61M 16/105 |
| 2017/0266403 | A1 | 9/2017 | Prentice et al. | |
| 2017/0348505 | A1 * | 12/2017 | Doo | A61M 16/0057 |

FOREIGN PATENT DOCUMENTS

| | | | |
|---|---|---|---|
| JP | 2008-543473 | A | 12/2008 |
| JP | 2011-240174 | A | 12/2011 |
| JP | 2012-517850 | A | 8/2012 |
| JP | 2014-526319 | A | 10/2014 |
| JP | 2016-034411 | A | 3/2016 |
| JP | 2017-170166 | A | 9/2017 |
| JP | 2018-108380 | A | 7/2018 |

OTHER PUBLICATIONS

Written Opinion issued for PCT/JP2020/012250 dated Apr. 21, 2020.

* cited by examiner

CPAP APPARATUS

CROSS REFERENCE TO RELATED APPLICATION

This is a continuation of International Application No. PCT/JP2020/012250 filed on Mar. 19, 2020 which claims priority from Japanese Patent Application No. 2019-082052 filed on Apr. 23, 2019. The contents of these applications are incorporated herein by reference in their entireties.

BACKGROUND

Technical Field

The present disclosure relates to a CPAP (Continuous Positive Airway Pressure) apparatus that delivers air sucked in the apparatus to the airway of a user.

A continuous positive airway pressure (CPAP) apparatus (referred to below as a CPAP apparatus) that supplies a fluid to a user has been used for treatment of sleep-related disorders such as obstructive sleep apnea (OSA). The CPAP apparatus includes an air-sending apparatus that contains a fan and supplies the fluid (for example, air) to a mask that is equipped on the mouth or nose of the user from the air-sending apparatus at pressure higher than the atmospheric pressure to open an airway (see, for example, Patent Document 1).

Patent Document 1: Japanese Unexamined Patent Application Publication No. 2016-34411

BRIEF SUMMARY

It is known that humidification of the air that is supplied to the user is beneficial to the user. For this reason, it is thought that a humidification function is fulfilled. The CPAP apparatus needs to be continuously used every day. Accordingly, it is necessary to carry the CPAP apparatus, for example, in the case where the user stays away from home overnight. For this reason, the CPAP apparatus needs to have a decreases size and weight. However, the humidifier poses a risk to decrease in the portability of the apparatus.

The present disclosure provides a CPAP apparatus that has a humidification function and that has high portability.

A CPAP apparatus according to an aspect of the present disclosure is a CPAP apparatus that delivers air sucked in the apparatus to an airway of a user. The CPAP apparatus includes a first unit and a second unit on and from which the first unit is mountable and removable. The first unit includes a first housing that has a first inlet and a first outlet, an air-sending device that discharges, via the first outlet, air that is introduced via the first inlet, and a first control unit that controls the air-sending device. The second unit includes a second housing that has a second inlet and a second outlet, a humidifier that humidifies air that is introduced via the second inlet, and a second control unit that controls the humidifier. In a first use state in which the first unit is mounted on the second unit, the second inlet is connected to the first outlet, and a tube via which air is supplied to the user is connected to the second outlet. In a second use state in which the second unit is not mounted on the first unit, the tube is connected to the first outlet.

According to an aspect of the present disclosure, a CPAP apparatus that has a humidification function and that has high portability can be provided.

DETAILED DESCRIPTION

Figure 1:
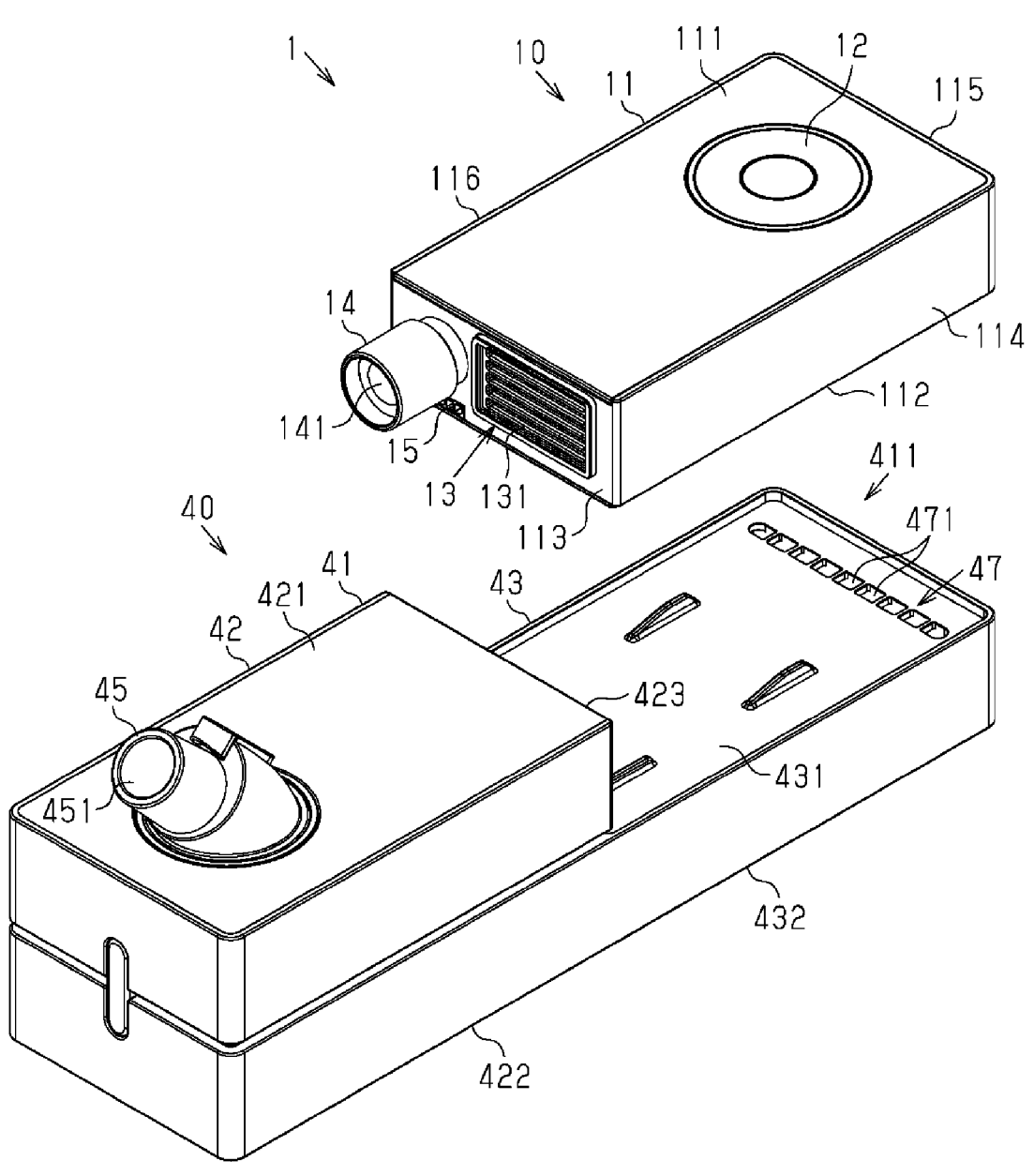
FIG. 1 is a perspective view of a body unit and a base unit in a CPAP apparatus.

An embodiment will now be described.

As illustrated in FIG. 1 to FIG. 8, a CPAP apparatus 1 includes a body unit 10 that serves as a first unit and a base unit 40 that serves as a second unit. The body unit 10 includes an air-sending device 22 that serves as a main component. The base unit 40 includes a humidifier 51 that serves as a main component.

The body unit 10 is mountable on and removable from the base unit 40.

According to the present embodiment, the CPAP apparatus 1 can be used in a first use state or in a second use state. The first use state is a state in which the body unit 10 is mounted on the base unit 40. The second use state is a state in which the body unit 10 is not mounted on the base unit 40.

In the first use state, the body unit 10 and the base unit 40 are used. In the second use state, only the body unit 10 is used, but the base unit 40 is not used.

The CPAP apparatus 1 according to the present embodiment becomes highly convenient, for example, when not only being at home but also staying away from home overnight in a manner in which the CPAP apparatus 1 includes multiple units, and the multiple units are configured to be mountable on and removable from each other. The CPAP apparatus 1 can be used in the first use state described above when being at home in a manner in which the body unit 10 is mounted on the base unit 40. In the first use state, the body unit 10 is mounted on the base unit 40, and consequently, the CPAP apparatus 1 that includes the humidifier 51 can supply humidified air to a user.

The CPAP apparatus 1 can be used in the second use state in which the body unit 10 is not mounted on the base unit 40, for example, when staying away from home overnight. In the second use state, the body unit 10 alone functions as the CPAP apparatus 1. Accordingly, only the body unit 10 suffices to be carried, and high portability is achieved. The CPAP apparatus 1, however, can be used in the second use state when being at home.

Figure 2:
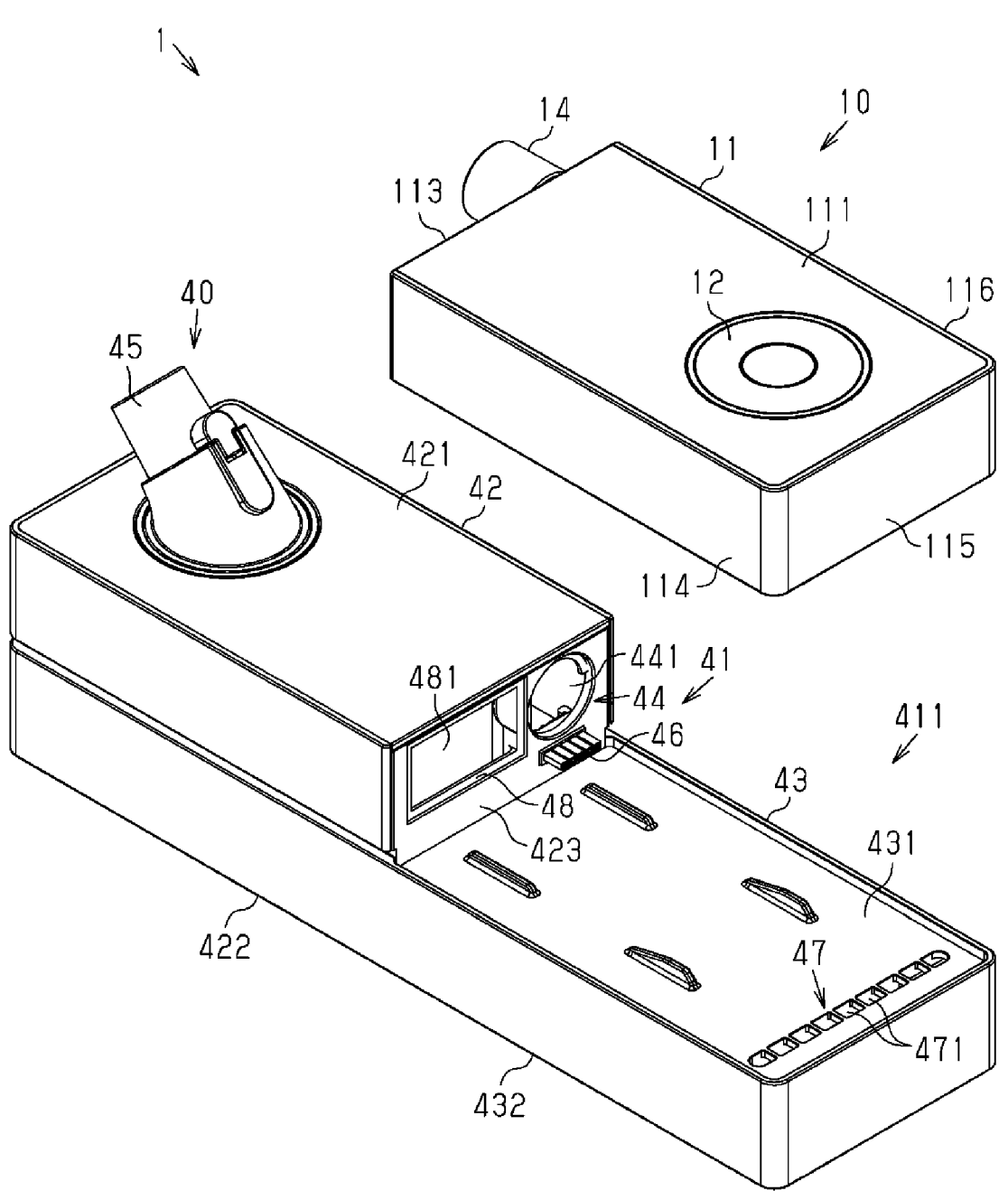
FIG. 2 is a perspective view of the CPAP apparatus viewed at a different angle.
Figure 3:
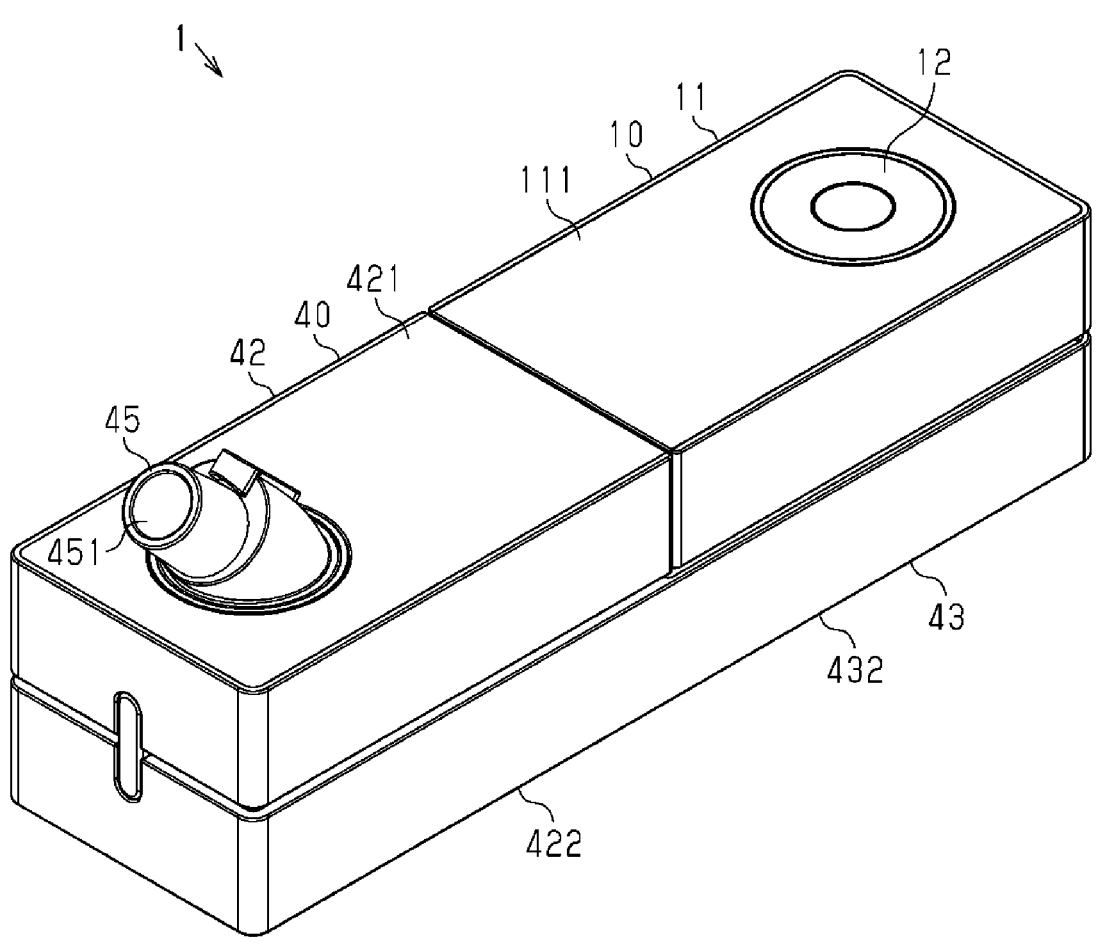
FIG. 3 is a perspective view of the base unit that is mounted on the body unit.

As illustrated in FIG. 1 to FIG. 3, the body unit 10 has a substantially rectangular cuboid shape that is flat, and the outer shell thereof includes a first housing 11. As used here, the terms "substantially rectangular" includes rectangular shapes with rounded corners, such as is illustrated in FIG. 1 to FIG. 3, as well as those without rounded corners.

The first housing 11 has an upper surface 111 and a lower surface 112 that face away from each other in a thickness direction and four side surfaces 113, 114, 115, and 116 that connect the upper surface 111 and the lower surface 112 to each other.

The upper surface 111 is an operation surface on which an operation unit 12 is disposed. The operation unit 12 includes an annular member and multiple switches that are switched on or off by the member. For example, setting values can be changed by switching on or off the switches of the operation unit 12 that is annular.

The lower surface 112 is a placement surface that is placed on the base unit 40 in the first use state and that is placed on, for example, a floor surface or a table in the second use state. The side surface 113 is a connection surface that is connected to the base unit 40 in the first use state and is referred to below as the first connection surface 113. The side surface 113 is perpendicular to the upper surface 111 and the lower surface 112.

A first introduction portion 13 and a first discharge portion 14 are disposed on the first connection surface 113 of the first housing 11. The first housing 11 has a first inlet 131 via which air outside the first housing 11 is introduced into the first housing 11 by the first introduction portion 13 and a first outlet 141 via which the air inside the first housing 11 is discharged to the outside by the first discharge portion 14. A first connection portion 15 that electrically connects the body unit 10 and the base unit 40 to each other is disposed in the first connection surface 113 of the first housing 11. According to the present embodiment, the first connection portion 15 electrically connects the body unit 10 and the base unit 40 to each other. According to the present embodiment, the first connection portion 15 is a connector that includes a terminal that is connected to or disconnected from a second connection portion 46 of the base unit 40.

As illustrated in FIG. 1 to FIG. 3, the base unit 40 includes a second housing 41. The second housing 41 includes a humidification portion 42 that includes the humidifier 51 illustrated in FIG. 5 and FIG. 7 and a placement portion 43 on which the body unit 10 is placed.

The humidification portion 42 is thicker than the placement portion 43. A lower surface 422 of the humidification portion 42 and a lower surface 432 of the placement portion 43 are flush with each other and are continuous with each other. Accordingly, the position of an upper surface 431 of the humidification portion 42 is higher than the position of an upper surface 421 of the placement portion 43. The second housing 41 is formed by the humidification portion 42 and the placement portion 43 into a substantially rectangular cuboid shape that is elongated and that has a notch portion 411 as a portion in a longitudinal direction. In the first use state, the lower surfaces 422 and 432 are placement surfaces that are placed on, for example, a floor surface or a table.

A second discharge portion 45 is disposed on the upper surface 421 of the humidification portion 42. The second housing 41 has a second outlet 451 via which air inside the second housing 41 is discharged by the second discharge portion 45. In the first use state, an air tube 2 (see FIG. 4A and FIG. 4B) is connected to the second discharge portion 45 (the second outlet 451). The body unit 10 is placed on the upper surface 431 of the placement portion 43. A difference between the height of the upper surface 421 of the humidification portion 42 and the height of the upper surface 431 of the placement portion 43 corresponds to the thickness of the first housing 11 of the body unit 10.

A side surface of the humidification portion 42 that faces the notch portion 411 is a second connection surface 423 to which the body unit 10 is connected.

A second introduction portion 44 is disposed in the second connection surface 423. The second housing 41 has a second inlet 441 via which air outside the second housing 41 is introduced by the second introduction portion 44. The second connection portion 46 is disposed in the second connection surface 423. The second connection portion 46 is connected to the first connection portion 15 of the body unit 10 in a manner in which the body unit 10 is mounted on the base unit 40. According to the present embodiment, the second connection portion 46 is a connector that includes a terminal that is connected to or disconnected from the first connection portion 15.

The first connection portion 15 and the second connection portion 46 are used to electrically connect or disconnect the body unit 10 and the base unit 40 to each other or from each other. According to the present embodiment, the first connection portion 15 and the second connection portion 46 are used to supply power to the base unit 40 and to transmit data or receive data by using a digital signal. The power can be supplied, and the data can be transmitted or received by using different connection portions. For example, non-contact power supply and near field communication, for example, can be used at the same time.

A third introduction portion 47 is disposed in the upper surface 431 of the placement portion 43 of the second housing 41 described above. The second housing 41 has multiple third inlets 471 via which air outside the second housing 41 is introduced by the third introduction portion 47. A fourth introduction portion 48 is disposed in the second connection surface 423 of the second housing 41. The second housing 41 has a third outlet 481 via which air is discharged from the second housing 41 by the fourth introduction portion 48.

The body unit 10 is located in the notch portion 411 of the base unit 40, and consequently, the lower surface 112 of the first housing 11 and the upper surface 431 of the placement portion 43 of the second housing 41 face each other, and the first connection surface 113 of the first housing 11 and the second connection surface 423 of the second housing 41 face each other. The first outlet 141 that is formed on the first connection surface 113 of the first housing 11 and the second inlet 441 that is formed in the second connection surface 423 of the second housing 41 are connected to each other. The first inlet 131 that is formed in the first connection surface 113 of the first housing 11 and the third outlet 481 that is formed in the second connection surface 423 of the second housing 41 are connected to each other.

Consequently, the CPAP apparatus 1 has a substantially rectangular cuboid shape as a whole. The air introduced into the second housing 41 by the third inlets 471 of the second housing 41 is introduced into the first housing 11 via the third outlet 481 of the second housing 41 and the first inlet 131 of the first housing 11. The air in the first housing 11 is introduced into the second housing 41 via the first outlet 141 of the first housing 11 and the second inlet 441 of the second housing 41. The air is discharged to the outside via the second outlet 451 of the second housing 41.

The first connection surface 113 of the first housing 11 is exposed to the outside in a state in which the body unit 10 is not mounted on the base unit 40. For this reason, the first inlet 131 and the first outlet 141 that are formed in the first connection surface 113 of the first housing 11 are open to the outside. Consequently, the body unit 10 introduces the air outside the first housing 11 into the first housing 11 by the first inlet 131 and discharges the air in the first housing 11 to the outside via the first outlet 141. That is, the body unit 10 alone functions as the CPAP apparatus. As clear from FIG. 1 to FIG. 3, the volume of the body unit 10 itself is smaller than the total volume of the body unit 10 and the base unit 40.

Figure 4A:
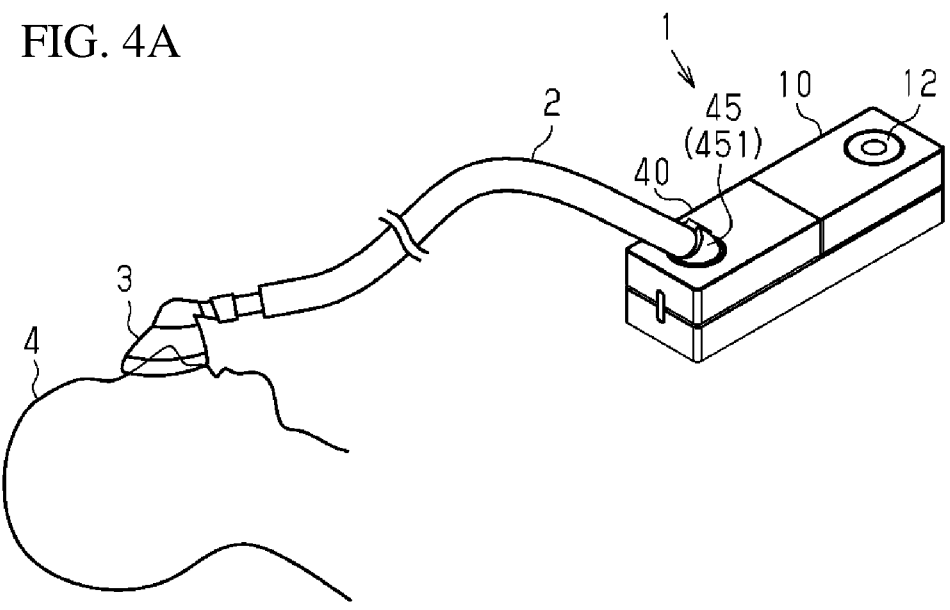
FIG. 4A schematically illustrates a first use state of the CPAP apparatus, and FIG. 4B schematically illustrates a second use state of the CPAP apparatus.
Figure 4B:
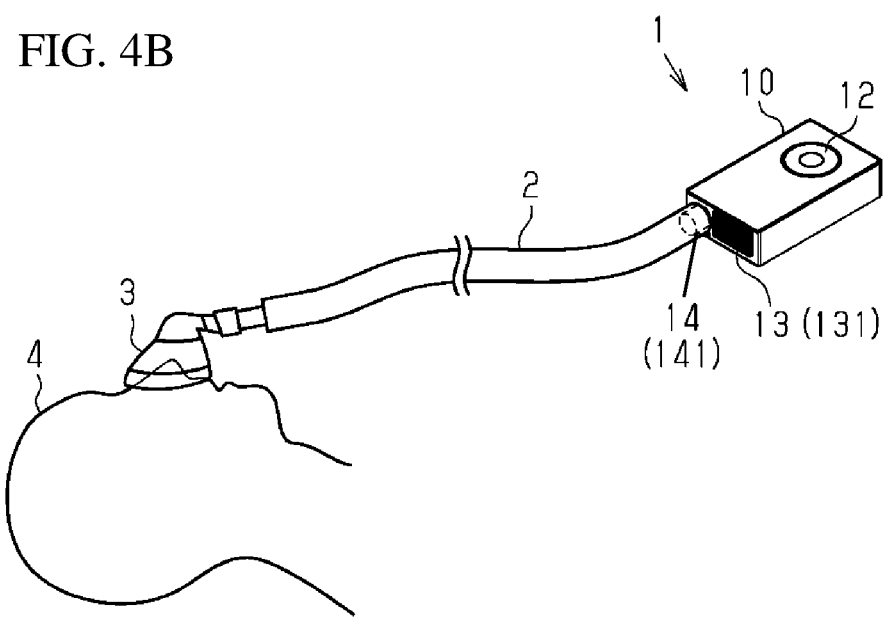

FIG. 4A and FIG. 4B schematically illustrate the use states of the CPAP apparatus 1 according to the present embodiment. FIG. 4A illustrates the first use state. FIG. 4B illustrates the second use state.

As illustrated in FIG. 4A, in the first use state, the CPAP apparatus 1 is used with the body unit 10 mounted on the base unit 40. In this case, a first end portion of the air tube 2 is connected to the second discharge portion 45 that is included in the base unit 40, and a second end portion of the air tube 2 is connected to a mask 3. For example, the mask 3 is equipped so as to cover the nose or mouth of a user 4.

In the first use state, the air-sending device 22 that is included in the body unit 10 is driven, and consequently, air is sucked into the CPAP apparatus 1 via the third inlets 471 that are included in the base unit 40, and the air in the CPAP apparatus 1 is discharged to the outside via the second discharge portion 45 (the second outlet 451) that is included in the base unit 40. Consequently, the air is delivered to the airway of the user 4 via the air tube 2 and the mask 3.

As illustrated in FIG. 4B, in the second use state, the body unit 10 of the CPAP apparatus 1 is not mounted on the base unit 40, that is, only the body unit 10 is used. In this case, the first end portion of the air tube 2 is connected to the first discharge portion 14 that is included in the body unit 10, and the second end portion of the air tube 2 is connected to the mask 3. For example, the mask 3 is equipped so as to cover the nose or mouth of the user 4.

In the second use state, the air-sending device 22 that is included in the body unit 10 is driven, and consequently, air is sucked into the CPAP apparatus 1 via the first introduction portion 13 (the first inlet 131) that is included in the body unit 10, and the air in the CPAP apparatus 1 is discharged to the outside via the first discharge portion 14 (the first outlet 141) that is included in the body unit 10. Consequently, the air is delivered to the airway of the user 4 via the air tube 2 and the mask 3.

The structure of function blocks of the CPAP apparatus 1 according to the present embodiment will now be described.

Figure 5:
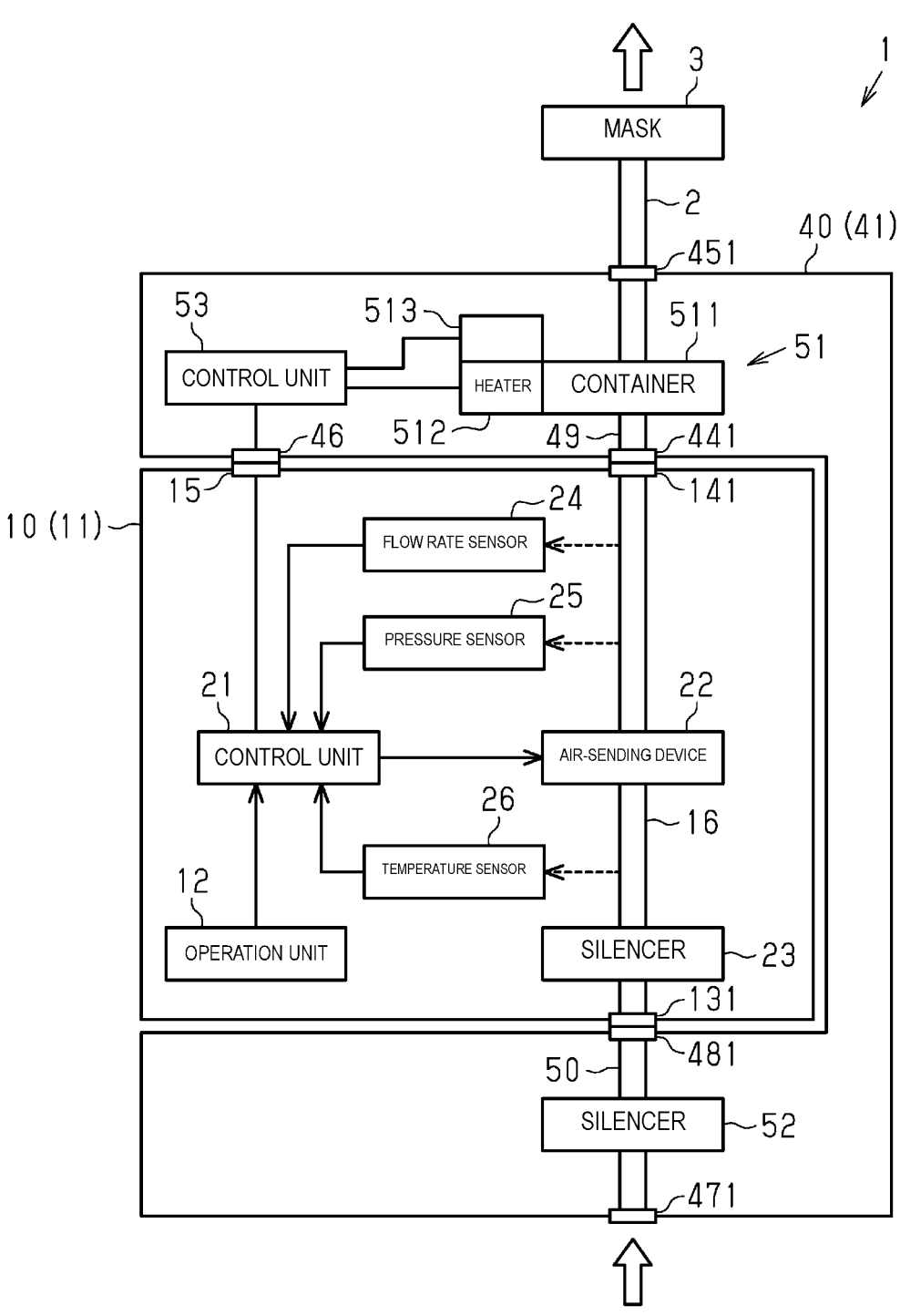
FIG. 5 illustrates the structure of a function block of the CPAP apparatus in the first use state.
Figure 6:
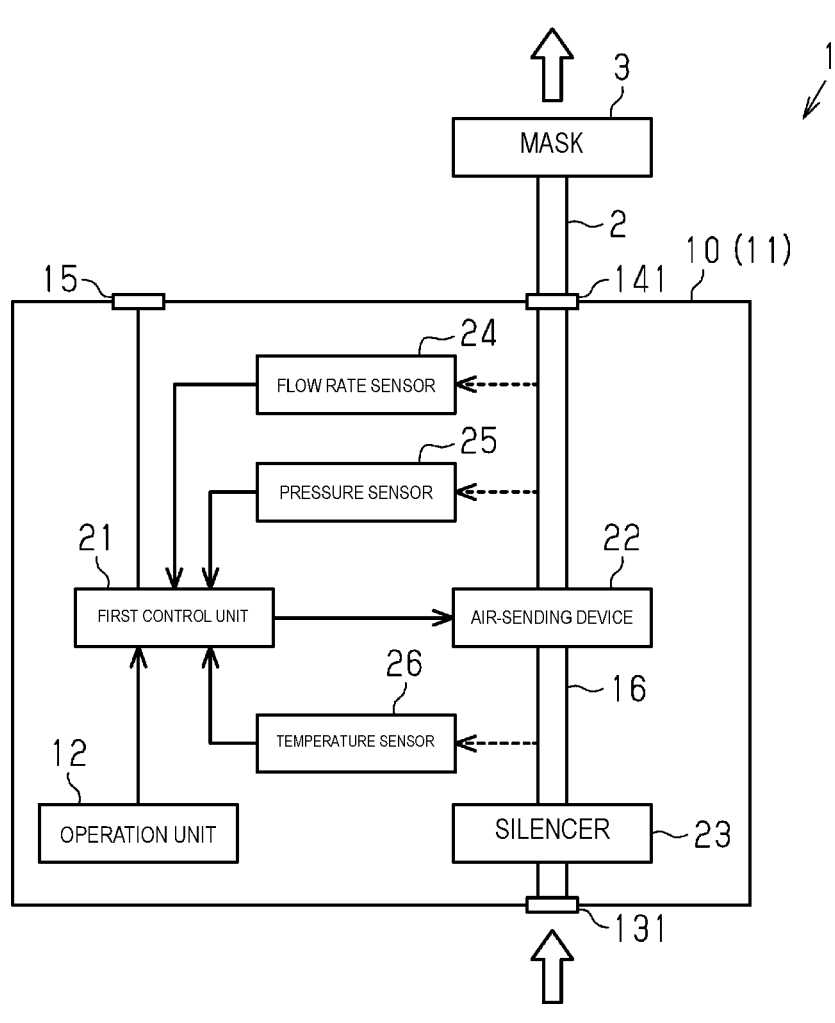
FIG. 6 illustrates the structure of a function block of the CPAP apparatus in the second use state.

FIG. 5 illustrates the structure of a function block of the CPAP apparatus 1 according to the present embodiment in the first use state. FIG. 6 illustrates the structure of a function block of the CPAP apparatus 1 in the second use state.

As illustrated in FIG. 5 and FIG. 6, the body unit 10 of the CPAP apparatus 1 includes a first control unit 21, the operation unit 12, the air-sending device 22, a silencer 23, a flow rate sensor 24, a pressure sensor 25, and a temperature sensor 26. The base unit 40 includes the humidifier 51, a silencer 52, and a second control unit 53. The first control unit 21 and the second control unit 53 have a digital connection to each other. Consequently, the first control unit 21 and the second control unit 53 can communicate with each other.

The body unit 10 has a first flow path 16 between the first inlet 131 and the first outlet 141. On the first flow path 16, the air-sending device 22 is disposed. The air-sending device 22 (e.g., a blower) can include a fan, such as a centrifugal fan and a drive motor that drives the fan. The air-sending device 22 is installed in an air-sending device chamber that is formed in the first housing 11. The air-sending device chamber corresponds to a part of the first flow path 16. The air-sending device chamber enables the air-sending device 22 to be disposed on the first flow path 16.

On the first flow path 16, the silencer 23 is disposed between the first inlet 131 and the air-sending device 22. The silencer 23 inhibits a noise (such as an operation noise of the drive motor or a wind noise of the fan) that is produced by the air-sending device 22 from leaking to a location outside the first housing 11.

On the first flow path 16, the pressure sensor 25, the flow rate sensor 24, and the temperature sensor 26 corresponding to a first temperature sensor are disposed. The pressure sensor 25 detects the pressure of air that is delivered by the air-sending device 22. The flow rate sensor 24 detects the flow rate of air between the air-sending device 22 and the air tube 2. The temperature sensor 26 detects the temperature (first temperature) of air outside the body unit 10 that is introduced.

The first control unit 21 includes main components, such as a central processing unit (CPU) that runs a program, a storage unit (a ROM: a read only memory/a RAM: a random access memory), a communication unit that has a communication function, and a drive unit that causes the air-sending device 22 to operate. The storage unit includes the ROM that stores data in a non-volatile manner and the RAM that stores data in a volatile manner. Examples of the data that is stored in the storage unit include data that is generated by running the program by the central processing unit, data that is inputted by using the operation unit 12, data that is measured by the various sensors described above, and data that is transmitted to and received from the outside by using the communication unit.

Processing in the central processing unit is performed by software that is run by the central processing unit and hardware. The software is stored in the storage unit in advance. In addition, reception of the operation of the operation unit 12, control of the drive motor of the air-sending device 22, and communication with the outside, for example, are achieved by the software.

According to the present embodiment, the first control unit 21 increases or decreases the rotational speed of the air-sending device 22 by implementing control such as feedback control or feedforward control, based on the value of the flow rate and the value of the pressure that are detected by the flow rate sensor 24 and the pressure sensor 25 and controls, for example, the amount of the air that is delivered. For example, the first control unit 21 determines the state of exhalation of the user, based on the values measured by the flow rate sensor 24 and the pressure sensor 25 and controls the value of the pressure of the air that is supplied to the user in synchronization with the state of exhalation. The first control unit 21 reports the value of the temperature that is detected by the temperature sensor 26 to the second control unit 53 of the base unit 40.

The second housing 41 of the base unit 40 has a second flow path 49 between the second inlet 441 and the second outlet 451 and a third flow path 50 between the third inlets 471 and the third outlet 481. On the second flow path 49, the humidifier 51 is disposed. The humidifier 51 humidifies air that flows along the second flow path 49 in the first use state. In this way, the CPAP apparatus 1 adds appropriate moisture to the air that is delivered to the airway of the user. According to the present embodiment, the humidifier 51 is a heat humidification apparatus.

As illustrated in FIG. 5, the humidifier 51 includes a container 511, a heater 512, and a temperature sensor 513 corresponding to a second temperature sensor. The container 511 is mountable on and removable from the second housing 41. The container 511 stores water. The container 511 includes an introduction tube in communication with the second inlet 441. Air is supplied to the interior of the container 511 via the introduction tube. The container 511 includes a heater pad that is compatible with the heater 512. The heater 512 heats the water in the container 511. The temperature sensor 513 detects the temperature of the heater 512.

The second control unit 53 includes main components, such as a central processing unit (CPU) that runs a program, a storage unit (a ROM/a RAM), a communication unit, and a drive unit that causes the humidifier 51 to operate as in the first control unit 21 described above. The storage unit includes the ROM that stores data in a non-volatile manner and the RAM that stores data in a volatile manner. Examples of the data that is stored in the storage unit include data that is generated by running the program by the central processing unit, heater temperature that is measured by the temperature sensor 513, and data that is transmitted to and received from the first control unit 21 by using the communication unit in the first use state. The data that is received from the first control unit 21 includes the value of the temperature of the air that is measured by the temperature sensor 26 of the body unit 10. The data that is received from the first control unit 21 may include data that is inputted by using the operation unit 12.

Processing in the central processing unit is performed by software that is run by the central processing unit and hardware. The software is stored in the storage unit in advance. In addition, control of the heater 512 of the humidifier 51 and communication with the first control unit 21, for example, are achieved by the software.

According to the present embodiment, the second control unit 53 sets a target heater temperature for heating the water in the container 511, based on the temperature of the air that is received from the first control unit 21. For example, the second control unit 53 sets the target heater temperature by using a table or a calculation expression that is stored in, for example, the storage unit. The second control unit 53 drives the heater 512, based on the heater temperature that is detected by the temperature sensor 513 such that the heater temperature becomes the target heater temperature by implementing control such as feedback control or feedforward control. The heater 512 adjusts the temperature of the water in the container 511. When the heater temperature reaches the target heater temperature, the second control unit 53 controls the heater 512 such that the heater temperature is held at the target heater temperature. Subsequently, the temperature of the water in the container 511 becomes constant such that lost heat or heat of sublimation is compensated. Consequently, the humidity of the air that passes in the container 511 becomes appropriate humidity.

The second control unit 53 may stop the humidifier 51, that is, may stop the control of the heater 512, based on the temperature of the air that is received from the first control unit 21.

Figure 7:
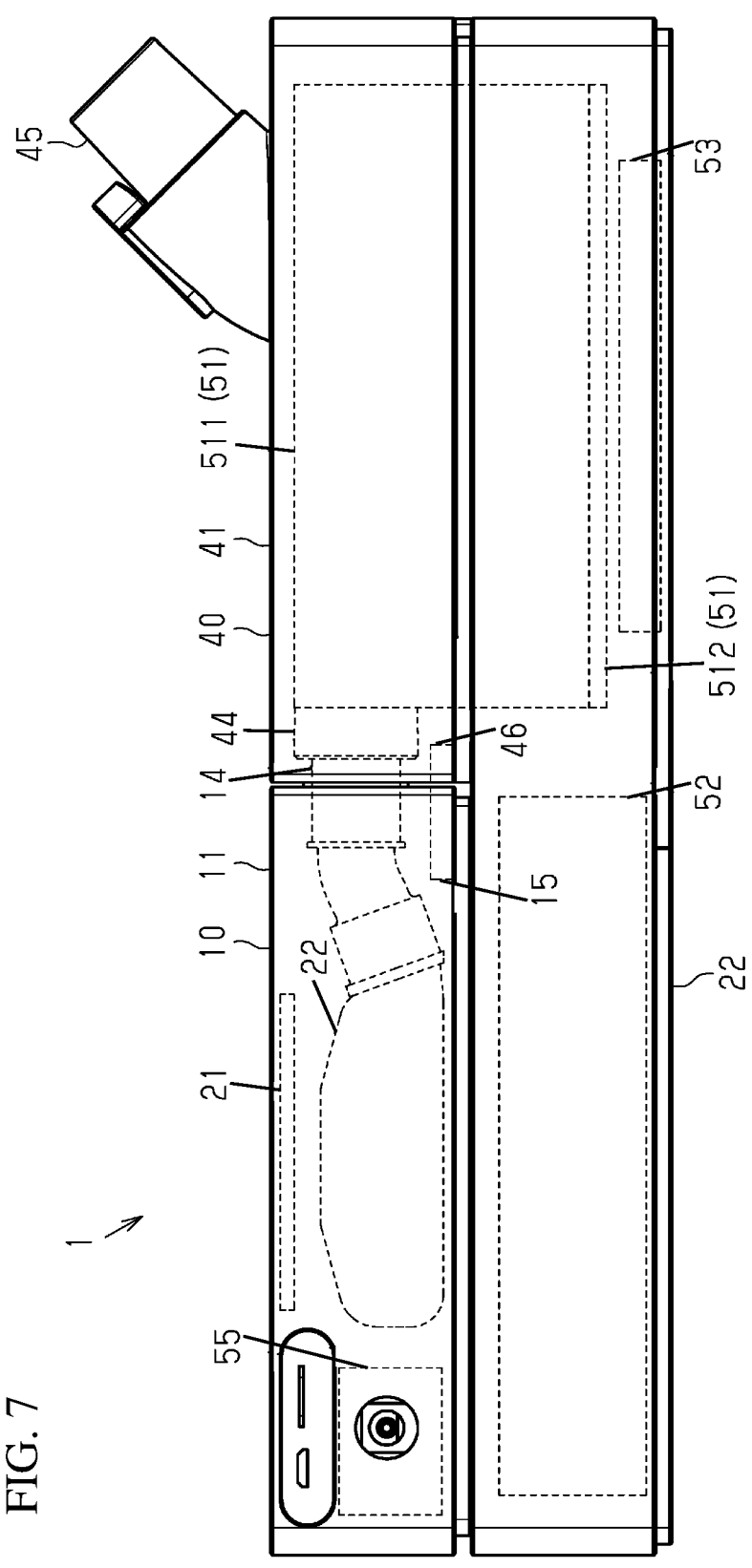
FIG. 7 illustrates a function block of the CPAP apparatus.
Figure 8:
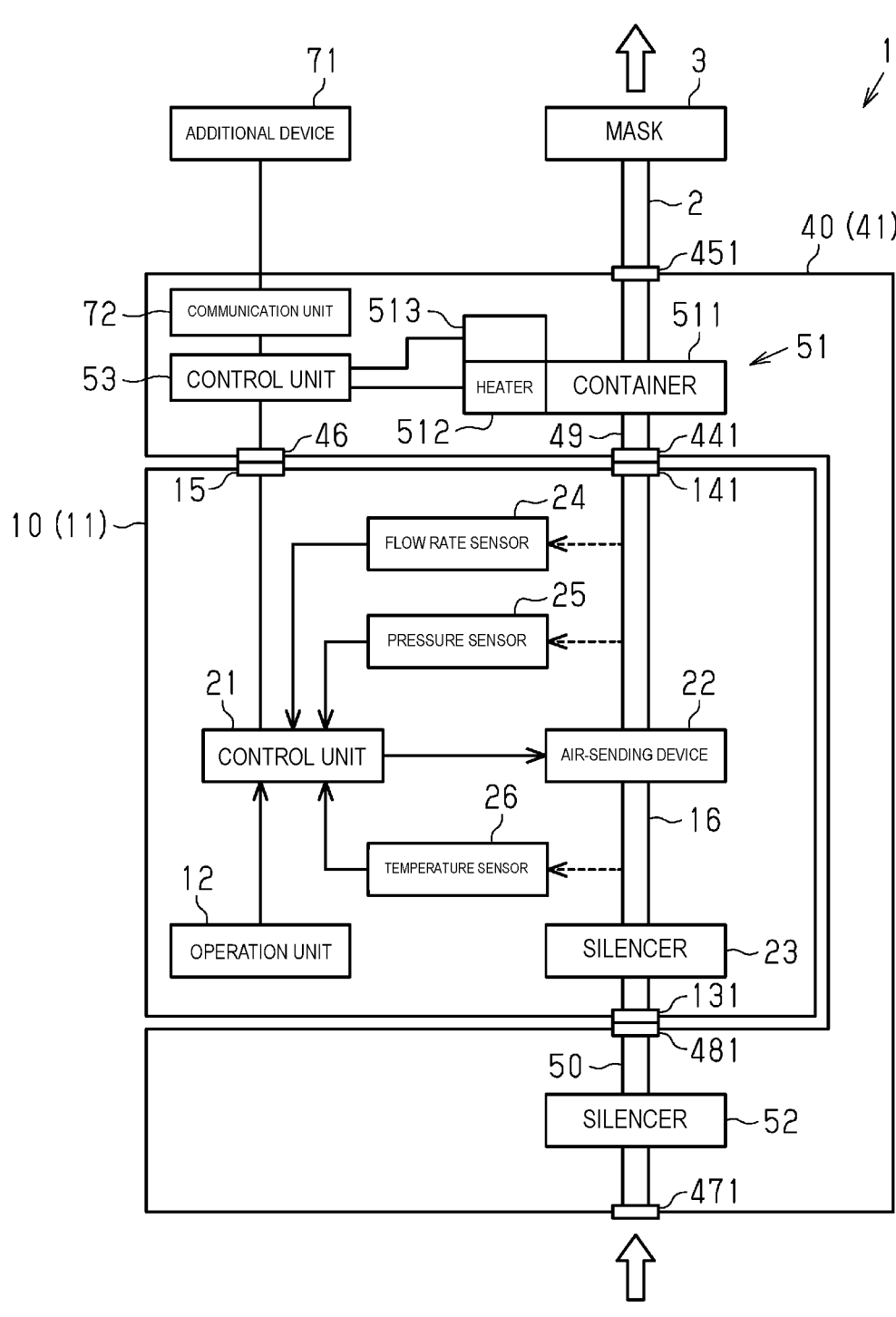
FIG. 8 is a block diagram illustrating an electrical structure of a CPAP apparatus according to a modification.

On the third flow path 50, the silencer 52 is disposed. As illustrated in FIG. 7, in the base unit 40, the silencer 52 is disposed in the placement portion 43 on which the body unit 10 is placed. The silencer 52 has a size slightly smaller than the size (shape) of the body unit 10. The more the volume of the silencer 52, the deeper the silence of the CPAP apparatus 1.

The silencer 52 includes, for example, a resonance tube into which the third flow path 50 sprits. The resonance tube has a meandering flow path. The resonance tube is referred to as a Helmholtz resonator or a resonator and has a function of attenuating a noise in a predetermined frequency band. The resonance tube attenuates a noise in a frequency band that is determined by the natural frequency.

As illustrated in FIG. 7, the body unit 10 includes a power supply unit 55. An AC adaptor, not illustrated, is connected to the power supply unit 55. The power supply unit 55 generates operating power that is needed for the body unit 10 and the base unit 40. The operating power is supplied to, for example, the second control unit 53 of the base unit 40 via the first connection portion 15 of the body unit 10 and the second connection portion 46 of the base unit 40.

According to the present embodiment, the body unit 10 has a first function, for example, an air-sending function, and the base unit 40 has a second function that differs from the first function, for example, a humidification function. The base unit 40 does not have the first function. The body unit 10 does not have the second function.

The action of the CPAP apparatus 1 described above will now be described.

The base unit 40 includes the humidifier 51 and the second control unit 53 that controls the humidifier 51. The humidifier 51 includes the container 511, the heater 512 that heats the water in the container 511, and the temperature sensor 513 that detects the heater temperature of the heater 512. The temperature sensor 513 has an analog connection to the second control unit 53.

If the humidifier 51 is controlled by the body unit 10, the temperature sensor 513 is connected to the first control unit 21 of the body unit 10 with the first connection portion 15 and the second connection portion 46 interposed therebetween, and the length of a wiring line through which an analog signal is transmitted increases. Consequently, the analog signal between the temperature sensor 513 and the first control unit 21 is likely to be affected by, for example, an extraneous noise against the wiring line, or a decrease in a signal level due to the resistance of the wiring line and contact resistance between the first connection portion 15 and the second connection portion 46.

As for the CPAP apparatus 1 according to the present embodiment, however, the base unit 40 includes the second control unit 53, and consequently, the temperature sensor 513 can be connected to the second control unit 53 at a short distance. For this reason, the length of a wiring line that connects the temperature sensor 513 and the second control unit 53 to each other is short, the influence of inductance or the resistance of the connecting wiring line, for example, is unlikely to be exerted, and the heater temperature can be measured with precision. In addition, the influence of a noise on, for example, the wiring line that connects the temperature sensor 513 and the second control unit 53 to each other can be reduced.

In the first use state in which the body unit 10 is mounted on the base unit 40, the second control unit 53 of the base unit 40 controls the humidifier 51 that is included in the base unit 40. Accordingly, the first control unit 21 of the body unit 10 controls the air-sending device 22 that is included in the body unit 10 and accepts the operation of the operation unit 12. Accordingly, the load of calculation of the first control unit 21 can be reduced to a level lower than that in the case of controlling the entire CPAP apparatus 1 by using the first control unit 21, and heat generation can be reduced.

As illustrated in FIG. 3, in the state in which the body unit 10 is mounted on the base unit 40, the body unit 10 is located a predetermined distance (for example, about 1.5 mm) away from the upper surface 431 of the placement portion 43 of the base unit 40. Consequently, the third inlets 471 (see FIG. 1 and FIG. 2) that are included in the base unit 40 are in communication with space outside the CPAP apparatus 1 via a gap between the base unit 40 and the body unit 10. Accordingly, direction is not limited, the air can be efficiently sucked, and a noise is inhibited from leaking via the third inlets 471 to the outside in a manner in which the body unit 10 is located so as to face the third inlets 471.

According to the present embodiment, the following effects are achieved as described above.

(1) The CPAP apparatus 1 can be used in the first use state described above when the CPAP apparatus 1 is at home in a manner in which the body unit 10 is mounted on the base unit 40. In the first use state, the body unit 10 is mounted on the base unit 40, and consequently, the CPAP apparatus 1 that includes the humidifier 51 can supply humidified air to the user. The CPAP apparatus 1 can be used in the second use state in which the body unit 10 is not mounted on the base unit 40, for example, when staying away from home overnight. In the second use state, the body unit 10 alone functions as the CPAP apparatus 1. Accordingly, only the body unit 10 suffices to be carried, and high portability is achieved.

(2) The CPAP apparatus 1 includes the body unit 10 and the base unit 40 on which the body unit 10 is mounted. The body unit 10 includes the air-sending device 22 and the first control unit 21 that controls the air-sending device 22. The base unit 40 includes the humidifier 51 and the second control unit 53 that controls the humidifier 51. The humidifier 51 includes the container 511, the heater 512 that heats the water in the container 511, and the temperature sensor 513 that detects the heater temperature of the heater 512. The temperature sensor 513 has the analog connection to the second control unit 53.

As for the CPAP apparatus 1 according to the present embodiment, the base unit 40 includes the second control unit 53, and consequently, the temperature sensor 513 can be connected to the second control unit 53 at a short distance. For this reason, the length of the wiring line that connects the temperature sensor 513 and the second control unit 53 to each other is short, the influence of inductance or the resistance of the connecting wiring line, for example, is unlikely to be exerted, and the heater temperature can be measured with precision. In addition, the influence of a noise on, for example, the wiring line that connects the temperature sensor 513 and the second control unit 53 to each other can be reduced.

(3) In the first use state in which the body unit 10 is mounted on the base unit 40, the second control unit 53 of the base unit 40 controls the humidifier 51 that is included in the base unit 40. Accordingly, the first control unit 21 of the body unit 10 controls the air-sending device 22 that is included in the body unit 10 and accepts the operation of the operation unit 12. Accordingly, the load of calculation of the first control unit 21 can be reduced to a level lower than that in the case of controlling the entire CPAP apparatus 1 by using the first control unit 21, and heat generation can be reduced.

(4) In the first use state in which the body unit 10 is mounted on the base unit 40, the body unit 10 is located a predetermined distance (for example, about 1.5 mm) away from the upper surface 431 of the placement portion 43 of the base unit 40. Consequently, the third inlets 471 (see FIG. 1 and FIG. 2) that are included in the base unit 40 are in communication with space outside the CPAP apparatus 1 via the gap between the base unit 40 and the body unit 10. Accordingly, direction is not limited, the air can be efficiently sucked, and a noise is inhibited from leaking via the third inlets 471 to the outside in a manner in which the body unit 10 is located so as to face the third inlets 471.

Modification

The embodiment described above may be carried out in the following aspects.

As for the base unit 40 according to the embodiment described above, as illustrated in FIG. 8, the second control unit 53 may be capable of communicating with an additional device 71. For example, the base unit 40 of the CPAP apparatus 1 includes a communication unit 72. For example, the communication unit 72 is connected to the additional device 71 of the CPAP apparatus 1 with a wired cable or wirelessly for communication. The second control unit 53 observes the state of the user by using the additional device 71 and transmits control information depending on the state of the user to the first control unit 21. The first control unit 21 controls the air-sending device 22, based on the control information.

An example of the additional device 71 can be a photographing device. In the case of the photographing device, the state information (posture) about the state of the user is photographed. Photograph data is transmitted to the second control unit 53 of the base unit 40 by using the communication unit 72. The second control unit 53 determines the state about the state of the user, based on the photograph data and transmits the result of determination to the first control unit 21 of the body unit 10. The first control unit 21 controls the air-sending device 22 depending on the received result of determination, that is, the state about the state of the user. The airway of the user is unlikely to close or is likely to close depending on the state about the state of the user (face down, sideways, and so on). For this reason, the state of the user is determined from the state, the pressure of the air that is supplied to the user, for example, is controlled by the first control unit 21, based on the result of determination, and the presence or absence of humidify, for example, is controlled by the second control unit 53. For example, in the case of posture in which the airway is unlikely to close, the value of positive pressure that is applied is decreased, and consequently, a load to the user can be reduced. The photographing device that serves as the additional device 71 may be assembled with the base unit 40. In this case, the communication unit 72 can be omitted.

An example of the additional device 71 can be an acceleration sensor. The acceleration sensor is mounted on, for example, a futon that the user uses. The state information about the state of the user (the frequency of turning over), for example, is monitored by using the acceleration sensor, and the air-sending device 22 and the humidifier 51 of the CPAP apparatus 1 are controlled depending on the result of monitoring.

As described above, a program for processing data that is obtained by an external apparatus uses a large capacity in the storage unit, and there is a need for the storage unit that has a large capacity. Data processing applies great load to the control unit. For this reason, the load of the first control unit 21 of the body unit 10 and the capacity of the storage unit can be reduced in a manner in which the second control unit 53 of the base unit 40 performs the processing.

According to the embodiment described above, the base unit 40 may include the temperature sensor 26 that detects the temperature of the air. The temperature sensor 26 that is included in the base unit 40 has an analog connection to the second control unit 53. Consequently, communication between the first control unit 21 and the second control unit 53 is reduced, and the processing load of the first control unit 21 can be reduced.

REFERENCE SIGNS LIST

1 . . . CPAP apparatus, 2 . . . tube, 3 . . . mask, 10 . . . body unit (first unit), 40 . . . base unit (second unit), 21 . . . first control unit, 22 . . . air-sending device, 131 . . . first inlet, 141 . . . first outlet, 441 . . . second inlet, 451 . . . second outlet, 471 . . . third inlet, 481 . . . third outlet, 51 . . . humidifier, 53 . . . second control unit.

The invention claimed is:

1. A continuous positive airway pressure (CPAP) apparatus that delivers air drawn in the apparatus to an airway of a user, the CPAP apparatus comprising:

a body; and a base on which the body is mountable, and from which the body is removable, wherein the body comprises a first housing, a first inlet and a first outlet, a blower configured to discharge, via the first outlet, air that is introduced to the blower via the first inlet, and a first controller configured to control the blower, wherein the base comprises a second housing, a second inlet and a second outlet, a third inlet and a third outlet, a humidifier configured to humidify air that is introduced to the humidifier via the second inlet, and a second controller configured to control the humidifier, wherein, when the CPAP apparatus is in a first use state in which the body is mounted on the base, the third outlet is connected to the first inlet, the first outlet is connected to the second inlet, and a tube through which air is delivered to the user is connected to the second outlet, such that air is drawn into the apparatus via the third inlet, and passes from the base to the body to the base to the tube, and wherein, when the CPAP apparatus is in a second use state in which the body is not mounted on the base, air is drawn into the apparatus via the first inlet and the tube is connected to the first outlet.

2. The CPAP apparatus according to claim 1, wherein the first controller and the second controller are digitally connected to each other and are configured to receive digital signals from each other.

3. The CPAP apparatus according to claim 1, wherein the body further comprises a first temperature sensor that has an analog connection to the first controller, and that is configured to detect a temperature of air that is introduced into the first housing by the blower, and wherein when the CPAP apparatus is in the first use state, the first controller is configured to report a first temperature that is detected by the first temperature sensor to the second controller, and the second controller is configured to control the humidifier based on the first temperature that is received from the first controller.

4. The CPAP apparatus according to claim 3, wherein the humidifier comprises a container that is configured to store water, a heater that is configured to heat the water in the container, and a second temperature sensor that is configured to detect a heater temperature of the heater, and wherein the second controller is configured to set a target heater temperature based on the first temperature, and to control the heater such that the heater temperature that is detected by the second temperature sensor becomes equal to the target heater temperature.

5. The CPAP apparatus according to claim 1, wherein the body further comprises a pressure sensor that is configured to detect a pressure of air that is discharged by the blower, and a flow rate sensor that is configured to detect a flow rate of air between the blower and the tube, and wherein the first controller is configured to control the blower based on a value of the pressure that is detected by the pressure sensor, and a value of the flow rate that is detected by the flow rate sensor.

6. The CPAP apparatus according to claim 5, wherein the second controller is configured to communicate with an additional device that is configured to detect a state of the user, and to transmit state information to the first controller, the state information representing the state of the user that is detected by the additional device, and wherein the first controller is configured to control the blower based on the value of the pressure, the value of the flow rate, and the state information.

7. A continuous positive airway pressure (CPAP) apparatus that delivers air sucked in the apparatus to an airway of a user, the CPAP apparatus comprising:

a body; and a base on which the body is mountable, and from which the body is removable, wherein the body comprises a first housing that has a first inlet and a first outlet, a blower configured to discharge, via the first outlet, air that is introduced via the first inlet, and a first controller configured to control the blower, wherein the base comprises a second housing that has a second inlet and a second outlet, a humidifier configured to humidify air that is introduced via the second inlet, and a second controller configured to control the humidifier, wherein, when the CPAP apparatus is in a first use state in which the body is mounted on the base, the second inlet is connected to the first outlet, and a tube through which air is supplied to the user is connected to the second outlet, wherein, when the CPAP apparatus is in a second use state in which the body is not mounted on the base, the tube is connected to the first outlet, wherein the second housing has a third inlet and a third outlet that is connected to the first inlet when the CPAP apparatus is in the first use state, wherein the base further comprises a first temperature sensor that has an analog connection to the second controller, and that is configured to detect a temperature of air that is introduced into the second housing via the third inlet by the blower, and wherein when the CPAP apparatus is in the first use state, the second controller is configured to control the humidifier based on a first temperature that is detected by the first temperature sensor.

8. The CPAP apparatus according to claim 7, wherein the humidifier comprises a container that is configured to store water, a heater that is configured to heat the water in the container, and a second temperature sensor that is configured to detect a heater temperature of the heater, and wherein the second controller is configured to set a target heater temperature based on the first temperature, and to control the heater such that the heater temperature that is detected by the second temperature sensor becomes equal to the target heater temperature.

9. The CPAP apparatus according to claim 7, wherein the first controller and the second controller are digitally connected to each other and are configured to receive digital signals from each other.

10. The CPAP apparatus according to claim 7, wherein when the CPAP apparatus is in the first use state, the first controller is configured to report the first temperature that is detected by the first temperature sensor to the second controller, and the second controller is configured to control the humidifier based on the first temperature that is received from the first controller.

11. The CPAP apparatus according to claim 7,
wherein the body further comprises a pressure sensor that is configured to detect a pressure of air that is discharged by the blower, and a flow rate sensor that is configured to detect a flow rate of air between the blower and the tube, and
wherein the first controller is configured to control the blower based on a value of the pressure that is detected by the pressure sensor, and a value of the flow rate that is detected by the flow rate sensor.

12. The CPAP apparatus according to claim 11,
wherein the second controller is configured to communicate with an additional device that is configured to detect a state of the user, and to transmit state information to the first controller, the state information representing the state of the user that is detected by the additional device, and
wherein the first controller is configured to control the blower based on the value of the pressure, the value of the flow rate, and the state information.

* * * * *